US00PP28538P2

(12) United States Plant Patent
Thorup

(10) Patent No.: US PP28,538 P2
(45) Date of Patent: Oct. 17, 2017

(54) ***SALVIA* PLANT NAMED 'BALMIRDEPUR'**

(50) Latin Name: *Salvia greggii*
Varietal Denomination: Balmirdepur

(71) Applicant: Ball Horticultural Company, West Chicago, IL (US)

(72) Inventor: Troy Thorup, Chiang Mai (TH)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/330,151

(22) Filed: Aug. 16, 2016

(51) Int. Cl.
*A01H 5/02* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Audrey Charles

(57) ABSTRACT

A new and distinct cultivar of *Salvia* plant named 'Balmirdepur', characterized by its deep purple-violet colored flowers, medium green-colored foliage, and moderately vigorous, upright growth habit, is disclosed.

1 Drawing Sheet

Latin name of genus and species of plant claimed: *Salvia greggii.*

Variety denomination: 'Balmirdepur'.

BACKGROUND OF THE INVENTION

The present invention relates to a new and distinct cultivar of *Salvia* plant botanically known as *Salvia greggii* and hereinafter referred to by the cultivar name 'Balmirdepur'.

The new cultivar originated in a controlled breeding program in Guadalupe, Calif. during July 2013. The objective of the breeding program was the development of *Salvia* cultivars having large flowers and an upright-mounded growth habits.

The new *Salvia* cultivar is the result of self-pollination of the proprietary *Salvia greggii* breeding selection coded 13-2639-2, not patented, characterized by its medium purple-colored flowers, medium green-colored foliage, and moderately vigorous, upright growth habit. The new cultivar was discovered and selected as a single flowering plant within the progeny of the above stated self-pollination during July 2014 in a controlled environment in Guadalupe, Calif.

Asexual reproduction of the new cultivar by terminal stem cuttings since July 2014 in Guadalupe, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balmirdepur' as a new and distinct cultivar of *Salvia* plant:

1. Deep purple-violet colored flowers;
2. Medium green-colored foliage; and
3. Moderately vigorous, upright growth habit.

Plants of the new cultivar differ from plants of the parent primarily in having a flower color of a different shade of red and in having a shorter plant height.

Of the many commercially available *Salvia* cultivars, the most similar in comparison to the new cultivar is HEATWAVE Sparkle Sage 'EGGBEN004', U.S. Plant Pat. No. 24,154. However, in comparison, plants of the new cultivar differ from plants of 'EGGBEN004' in at least the following characteristics:

1. Plants of the new cultivar are shorter than plants of 'EGGBEN004';
2. Plants of the new cultivar have darker purple-colored flowers than plants of 'EGGBEN004'; and
3. Plants of the new cultivar have larger-sized flowers than plants of 'EGGBEN004'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balmirdepur'. The plants were approximately seven-months old and grown in one-gallon containers in a greenhouse in Elburn, Ill. Plants were given one pinch prior to transplant, one pinch two weeks after transplant, and a final pinch four weeks after transplant.

DETAILED BOTANICAL DESCRIPTION

Figure 1:
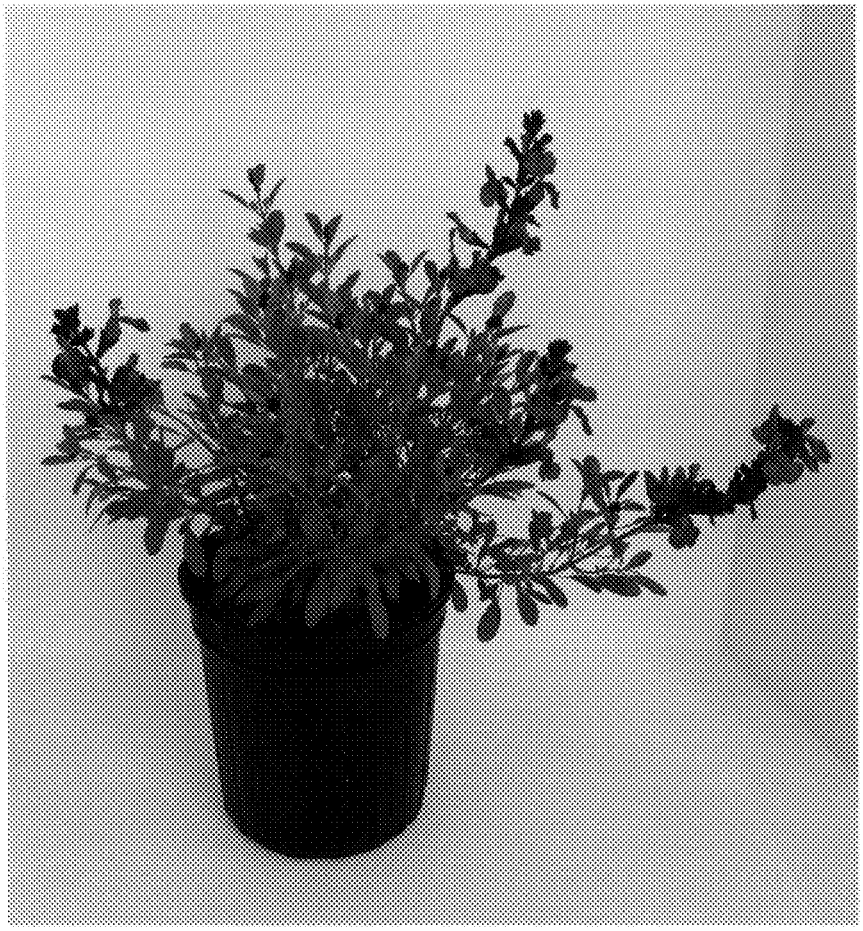
FIG. 1 illustrates a side view of the overall growth and flowering habit of 'Balmirdepur'.
Figure 2:
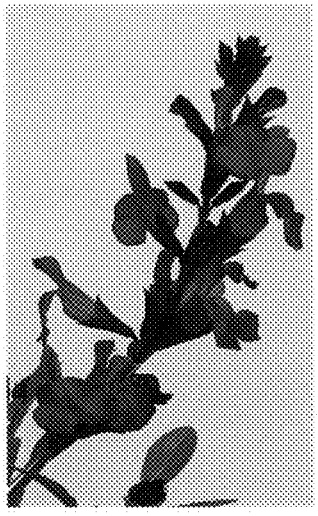
FIG. 2 illustrates a close-up view of an inflorescence of 'Balmirdepur'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2016 under natural light conditions in West Chicago, Ill.

The following descriptions and measurements describe plants produced from cuttings from stock plants and grown in a glass-covered greenhouse under conditions comparable to those used in commercial practice. The plants were grown utilizing a soilless growth medium in one-gallon containers for approximately seven months in Elburn, Ill. Plants were transplanted in late fall from rooted cuttings and were given one pinch prior to transplant, one pinch two weeks after transplant, and a final pinch four weeks after transplant. Greenhouse temperatures were maintained during the winter months at approximately 45° F. to 65° F. (7.2° C. to 18.3° C.) during the day and approximately 35° F. to 45° F. (1.7° C. to 7.2° C.) during the night. For the final 9 weeks, greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Salvia greggii* cultivar Balmirdepur.

Parentage:

*Female and male parent*.—Proprietary *Salvia greggii* breeding selection coded 13-2639-2, not patented.

Propagation:

*Type cutting*.—Terminal stem.

*Time to initiate roots*.—Approximately 10 to 12 days.

*Time to produce a rooted cutting*.—Approximately 35 to 42 days.

*Root description*.—Fine, fibrous white to light brown in color.

*Rooting habit*.—Freely branching.

Plant description:

*Commercial crop time*.—Approximately 8 to 10 weeks from a rooted cutting to finish in a 15 cm pot.

*Growth habit and general appearance*.—Moderately vigorous, upright-mounded growth habit.

*Plant type*.—Subshrub.

*Hardiness*.—USDA zones 7 to 9.

*Size*.—Height from soil level to top of plant plane: Approximately 30.0 cm. Width: Approximately 32.0 cm.

*Branching habit*.—Freely branching. Pinching enhances lateral branching. Quantity of branches per plant: Approximately 3 main basal branches and approximately 16 lateral branches.

*Branch*.—Shape: Square in cross section. Strength: Moderately strong, young growth flexible. Length to base of inflorescence: Approximately 16.5 cm. Diameter: Approximately 3.0 mm. Length of central internode: Approximately 2.5 cm. Texture: Densely pubescent. Color of young stems: 144A. Color of mature stems: 144A tinted with 187A in sun, becoming woody 200D with age.

Foliage description:

*General description*.—Quantity of leaves per branch: Approximately 14. Fragrance: Strong, sage-like. Form: Simple. Arrangement: Opposite.

*Leaves*.—Aspect: Acute to perpendicular angle to stem. Shape: Elliptic. Margin: Crenulate. Apex: Rounded. Base: Broadly attenuate to obtuse. Venation pattern: Pinnate. Length of mature leaf: Approximately 2.8 cm. Width of mature leaf: Approximately 1.4 cm. Texture of upper surface: Moderately pubescent. Texture of lower surface: Sparsely pubescent. Color of upper surface of young foliage: 144A and 137A with venation of 144A. Color of lower surface of young foliage: Closest to 138B with venation of slightly lighter than 146D. Color of upper surface of mature foliage: 137A with venation of 146D. Color of lower surface of mature foliage: Closest to 138B with venation of 146D.

*Petiole*.—Length: Approximately 1.2 cm. Diameter: Approximately 1.0 mm. Texture: Moderately pubescent. Color: 146C.

Flowering description:

*Flowering habit*.—'Balmirdepur' is freely flowering under outdoor growing conditions blooming from early spring through late summer.

*Lastingness of individual floret*.—Approximately 4 to 5 days.

Inflorescence description:

*General description*.—Type: Raceme with three to five florets per node, calyx persistent. Quantity of open inflorescences per plant: Approximately 4. Fragrance: Faint, sweet. Length or height of inflorescence: Approximately 8.0 cm to 11.5 cm. Width of inflorescence: Approximately 6.0 cm. Quantity of fully-open flowers per inflorescence: Approximately 10.

*Peduncle*.—Shape: Square in cross section. Strength: Strong. Aspect: Erect to approximately a 45° angle. Length: Approximately 3.5 cm. Diameter: Approximately 2.0 mm. Texture: Densely pubescent. Color: 144A with an overlay of N186A.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 1.2 cm. Diameter: Approximately 5.0 mm. Texture: Densely pubescent. Color: Calyx of 145A with a heavy overlay of N186A; petals of 93A to 93B with pubescence of N92C.

*Corolla*.—Shape: Bilabiate, lower lip having three lobes, based fused. Width: Approximately 1.8 cm. Length: Approximately 2.2 cm. Depth: Approximately 3.0 cm.

*Upper lip*.—Shape: Hooded. Margin: Entire. Apex: Rounded. Length from throat: Approximately 1.0 cm. Width: Approximately 4.0 mm. Texture of inner surface: Glabrous. Texture of outer surface: Densely pubescent. Color of pubescence: N92C. Color of inner surface when first and fully open: NN155D, translucent. Color of outer surface when first and fully open: N81A with N88A.

*Lower lip*.—Shape of central lobe: Obovate, cupped. Shape of lateral lobes: Oblong. Margin of central lobe: Shallowly scalloped. Margin of lateral lobes: Entire. Apex of central lobe: Emarginate to notched. Apex of lateral lobes: Rounded. Length from throat of central lobe: Approximately 1.3 cm. Width of central lobe: Approximately 1.8 cm. Length from throat of lateral lobes: Approximately 8.0 mm. Width of lateral lobes: Approximately 4.0 mm. Texture of upper surface: Glabrous. Texture of lower surface: Sparsely pubescent. Color of upper surface when first and fully open: Closest to N88A with an undertone of N81A near throat opening. Color of lower surface when first and fully open: Closest to N88B.

*Corolla tube*.—Length: Approximately 2.0 cm. Width: Approximately 7.0 mm. Texture of inner and outer surfaces: Glabrous. Color of inner surface: NN155D, translucent. Color of outer surface: N81A tinted with N88A.

*Calyx*.—Shape: Tubular. Length: Approximately 1.1 cm. Diameter: Approximately 8.0 mm.

*Sepals*.—Quantity per flower: 3, fused. Shape: Obovate. Margin: Entire. Apex: Acuminate. Length: Approximately 1.1 cm. Width: Two of approximately 3.0 mm and one of approximately 6.0 mm. Texture of inner and outer surfaces: Densely pubescent. Color of inner surface: 145A with an overlay of N92A at apex. Color of outer surface: N92D and 202A.

*Bracts*.—Quantity: One bract located at the base of each developing floret, bracts abscise as florets mature. Length: Approximately 8.0 mm. Width: Approximately 5.0 mm. Texture of inner surface: Glabrous. Texture of outer surface: Densely pubescent. Color of inner surface: NN155D with N88A at margins and 202A at tip. Color of outer surface: Closest to N88A with an overlay of 202A.

*Pedicel*.—Strength: Strong, flexible. Aspect: At an acute angle. Length: Approximately 7.0 mm. Diameter: Approximately 1.0 mm. Texture: Densely pubescent. Color of pubescence: 86A. Color: 202A.

*Reproductive organs*.—Androecium: Stamen quantity: 2 per flower, dorsifixed, strongly curved. Stamen length: Approximately 1.3 cm. Filament length: Approximately 1.2 cm. Filament color: NN155D with an overlay of N88A in center, opaque. Anther shape: Narrowly elliptic to oblong. Anther length: Approximately 2.0 mm. Anther color: N92B. Pollen amount: Abundant. Pollen color: NN155A. Gynoecium: Pistil quantity: 1 per flower, strongly curved. Pistil length: Approximately 3.0 cm. Stigma shape: Cleft, two-parted. Stigma length: 2.0 mm. Stigma color: N88A to N88B. Style length: Approximately 2.5 cm. Style color: NN155D, opaque with an overlay of N88B near stigma. Style texture: Glabrous with a vertical line of feather-like pubescence extending from the stigma for approximately 5.0 mm. Ovary length: Approximately 3.0 mm. Ovary color: N144A with 150D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balmirdepur', substantially as herein illustrated and described.

* * * * *